United States Patent
Hannemann

(10) Patent No.: US 8,718,744 B2
(45) Date of Patent: May 6, 2014

(54) IMAGING MEDICAL APPARATUS WITH A DEVICE TO IDENTIFY A PLANE IN SPACE

(75) Inventor: Thilo Hannemann, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 13/369,670

(22) Filed: Feb. 9, 2012

(65) Prior Publication Data

US 2012/0220863 A1   Aug. 30, 2012

(30) Foreign Application Priority Data

Feb. 25, 2011 (DE) .......................... 10 2011 004 747

(51) Int. Cl.
*A61B 5/05* (2006.01)

(52) U.S. Cl.
USPC .......................................... 600/425; 600/423

(58) Field of Classification Search
USPC ................................................. 600/425, 423
See application file for complete search history.

(56) References Cited

U.S. PATENT DOCUMENTS

| | | | |
|---|---|---|---|
| 4,392,182 A * | 7/1983 | Di Matteo | 362/5 |
| 5,058,967 A * | 10/1991 | Pairetti et al. | 359/861 |
| 5,782,842 A | 7/1998 | Kloess et al. | |
| 5,991,437 A * | 11/1999 | Migdal et al. | 382/154 |
| 6,142,653 A * | 11/2000 | Larson | 362/284 |
| 6,229,870 B1 * | 5/2001 | Morgan | 378/9 |
| 2005/0015004 A1 * | 1/2005 | Hertel et al. | 600/425 |
| 2009/0234370 A1 * | 9/2009 | Haras | 606/130 |

OTHER PUBLICATIONS

Matischek, "Laser Grundlagen und Anwendung" Thesis for Bruck/Mur Gymnasium (1995) pp. 1-29.

* cited by examiner

*Primary Examiner* — Tse Chen
*Assistant Examiner* — Lisa Kinnard
(74) *Attorney, Agent, or Firm* — Schiff Hardin LLP

(57) ABSTRACT

An imaging medical apparatus has at least one device to identify a plane in space. The device has: a light source that emits a fan-shaped light beam, the light source is rotatable around a light source rotation axis. The device also has a mirror that reflects the fan-shaped light beam, the mirror being rotatable around a mirror rotation axis and encompassing a mirror plane. The mirror rotation axis and the surface normal of the mirror plane enclose an angle greater than 0° and less than 90°.

7 Claims, 3 Drawing Sheets

IMAGING MEDICAL APPARATUS WITH A DEVICE TO IDENTIFY A PLANE IN SPACE

BACKGROUND OF THE INVENTION

1. Field of the Invention

The invention concerns an imaging medical apparatus with a device to identify a plane in space.

2. Description of the Prior Art

Devices to identify the attitude of planes are frequently used at imaging medical apparatuses or in connection with imaging medical apparatuses in order to mark or to illustrate the location and the direction of a medical instrument (a puncture needle, for example) based on image information of the body of a patient that is acquired with an imaging medical apparatus. Two such devices are most often used, wherein the optically visible intersection line of the planes of fan-shaped light beams identifies the direction of the instrument, and the intersection point of the intersection lines with the surface of the body of the patient identifies the puncture location for the instrument.

From DE 10 2008 013 615 A1, a computed tomography apparatus is known that has two fan lasers with which a guideline for a medical instrument can be marked. The fan lasers are arranged so as to be adjustable on the gantry of the computed tomography apparatus in order to be able to identify different planes in space or to mark different guidelines in space.

Furthermore, a device with two laser light beam localizers to mark a guide path of a puncture needle is described in DE 195 01 069 A1, wherein each laser light beam localizer emits a laser beam fanning out in a plane. The colors of the two fanned-out laser beams differ. The intersection line of the laser beams marks the guide path for the puncture needle. In addition to a diode laser that is rotatable around a first axis, each laser light beam localizer has a light-reflecting mirror that is rotatable around a second axis perpendicular to the first axis. With this light-reflecting mirror, the fanned-out laser beam of the diode laser can be reflected in a desired direction. This design—in particular the fixed attitude of the two axes relative to one another—limits the possibilities to generate identified planes in space.

Superstructures with a laser and deflector units in the form of tilted mirrors are described in Matischek, R.: Laser, Grundlagen und Anwendungen [Lasers, Fundamentals and Applications], Facharbeit aus der Physik, Bundesgymnasium und Bundesgymnasium Bruck/Mur, Reifeprüfung im Hauptttermin 1994/95, www.univie.ac.at/pluslucis/FBA/FBA95/Matischek/laser0.pdf.

SUMMARY OF THE INVENTION

An object of the invention is to provide an imaging medical apparatus of the aforementioned type such that the requirements to optimally extend the possibilities to identify planes in space are met.

According to the invention, this object is achieved by an imaging medical apparatus with at least one device to identify a plane in space, the device having a light source emitting a fan-shaped light beam, the light source being rotatable around a light source rotation axis, and a mirror that reflects the fan-shaped light beam, the mirror being rotatable around a mirror rotation axis and encompassing a mirror plane. The mirror rotation axis and the surface normal (surface perpendicular) of the mirror plane enclose an angle greater than 0° and less than 90°.

In the device according to the invention, thus, the rotation axis of the mirror and the surface normal of the mirror plane are tilted counter to one another so that, upon rotation, the mirror plane performs a wobble around the mirror rotation axis. The requirements to extend the spatial directions in which identifying planes can be generated thus are met.

In cooperation with the light source rotatable around the light source rotation axis (the fan-shaped light beam of which light source is directed onto the mirror), the tilted mirror produces a desired deflection or reflection of the fan-shaped light beam to identify a defined plane in space. A displacement in the direction of the fan-shaped laser beam additionally occurs, but this can be ignored since the identified plane or the plane to be identified is not changed thereby. Furthermore, an additional slight rotation of the fan-shaped laser beam, that can be compensated by rotation of the light source around the light source rotation axis, occurs due to the mirror.

The imaging medical apparatus can have two or more of the devices described above in order to be able to mark a guideline for a medical instrument by identifying two intersecting planes.

According to one embodiment of the invention, the light source and the mirror are aligned relative to one another such that the mirror rotation axis and the light source rotation axis are situated in one plane and together enclose an angle between 120° and 160°. The angle between the mirror rotation axis and the light source rotation axis advantageously amounts to 140°.

According to another embodiment of the invention, the light source is a laser light source, for example a fan laser.

Variants of the invention provide that the device has a first actuating drive [actuator; servo] to rotate the mirror plane around the mirror rotation axis, and a second actuating drive to rotate the light source around the light source rotation axis.

In an embodiment of the invention, the imaging medical apparatus is a computed tomography apparatus. The imaging medical apparatus can also be a C-arm x-ray apparatus, a magnetic resonance apparatus, a SPECT apparatus, a PET apparatus, an ultrasound apparatus or a combination apparatus made of at least two of the aforementioned apparatuses.

In the embodiment of the imaging medical apparatus as a computed tomography apparatus, this has a stationary part and a part rotatable around a system axis, at least two of the devices described in the preceding are arranged at the stationary part, and the two fan-shaped laser beams of the at least two devices intersect, at least to mark a guideline for a medical instrument.

DESCRIPTION OF THE PREFERRED EMBODIMENTS

Figure 1:
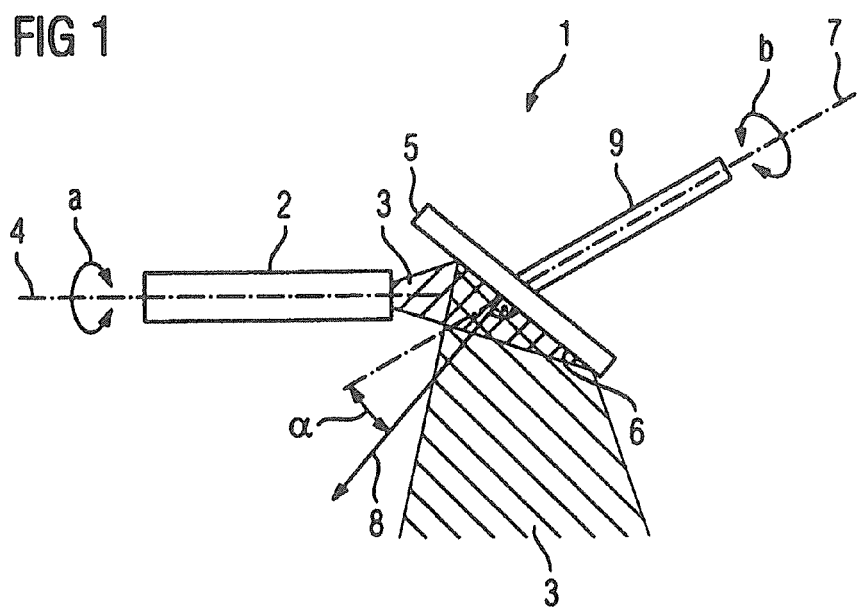
FIG. 1 schematically illustrates a device to identify a plane in space.

Identical or functionally identical elements in Figures are provided throughout with the same reference characters. The representations in Figures are schematic and not necessarily true to scale. The device and the computed tomography apparatus are discussed in the following and without limitation of the generality only insofar as is deemed necessary to understand the invention.

In a schematic representation, FIG. 1 shows a device 1 with a light source 2 that emits a fan-shaped light beam 3 and has a light source rotation axis 4. In the case of the present exemplary embodiment of the invention, the light source 2 is a fan laser. The fan laser is rotatable around the light source rotation axis 4 (see double arrow a).

A mirror 5 with a light-reflecting mirror plane 6 is associated with the fan laser. The mirror 5 is rotatable around a mirror rotation axis 7 (see double arrow b). According to the invention, the mirror 5 is tilted counter to the rotation axis 7 of the mirror, such that the mirror 5 performs a wobble around the mirror rotation axis 7 upon rotation. The tilt angle alpha—enclosed by the surface normal 8 of the mirror plane 6 and the mirror rotation axis 7 together—is plotted in FIG. 1 and normally amounts to between 5° and 25°. In FIG. 1, the mirror 5 is arranged fixed on a rotatable shaft 9 with which the mirror rotation axis 7 is registered.

The fan laser and the mirror 5 are arranged relative to one another such that, via rotation of the fan laser around the light source rotation axis 4 and via rotation of the mirror around the mirror rotation axis 7, the fan-shaped light beam 3 or light fan emanating from the fan laser and reflecting on the mirror plane 6 can identify a plurality of planes in space (in particular in a desired spatial region) depending on adjustment or, respectively, rotation setting of the fan laser and the mirror 5. This arrangement is advantageous when the set of planes to be identified requires only a limited lateral deflection of the laser fan. This is normally the case in imaging apparatuses since it is not planes of the entire space but rather only a defined working volume that should be or, respectively, must be identified.

Figure 2:
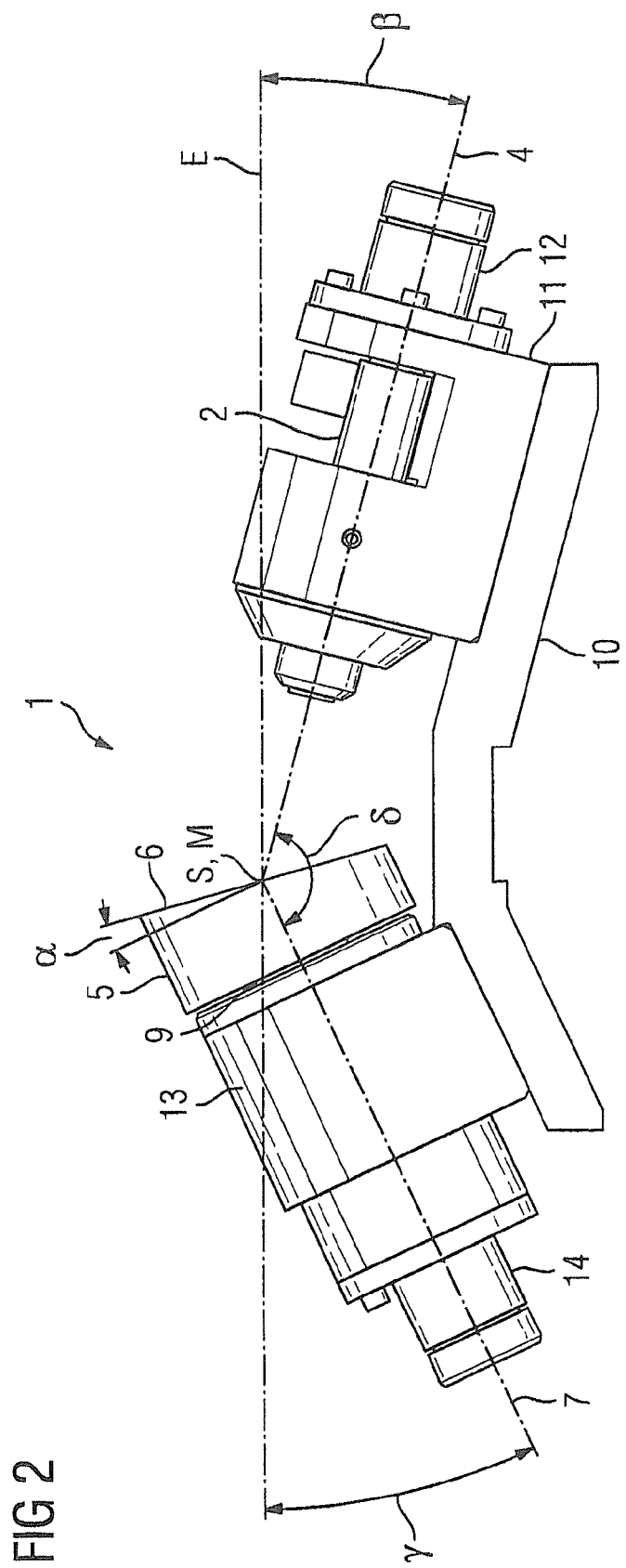
FIG. 2 shows an embodiment of a device to identify a plane in space in accordance with the invention.
Figure 3:
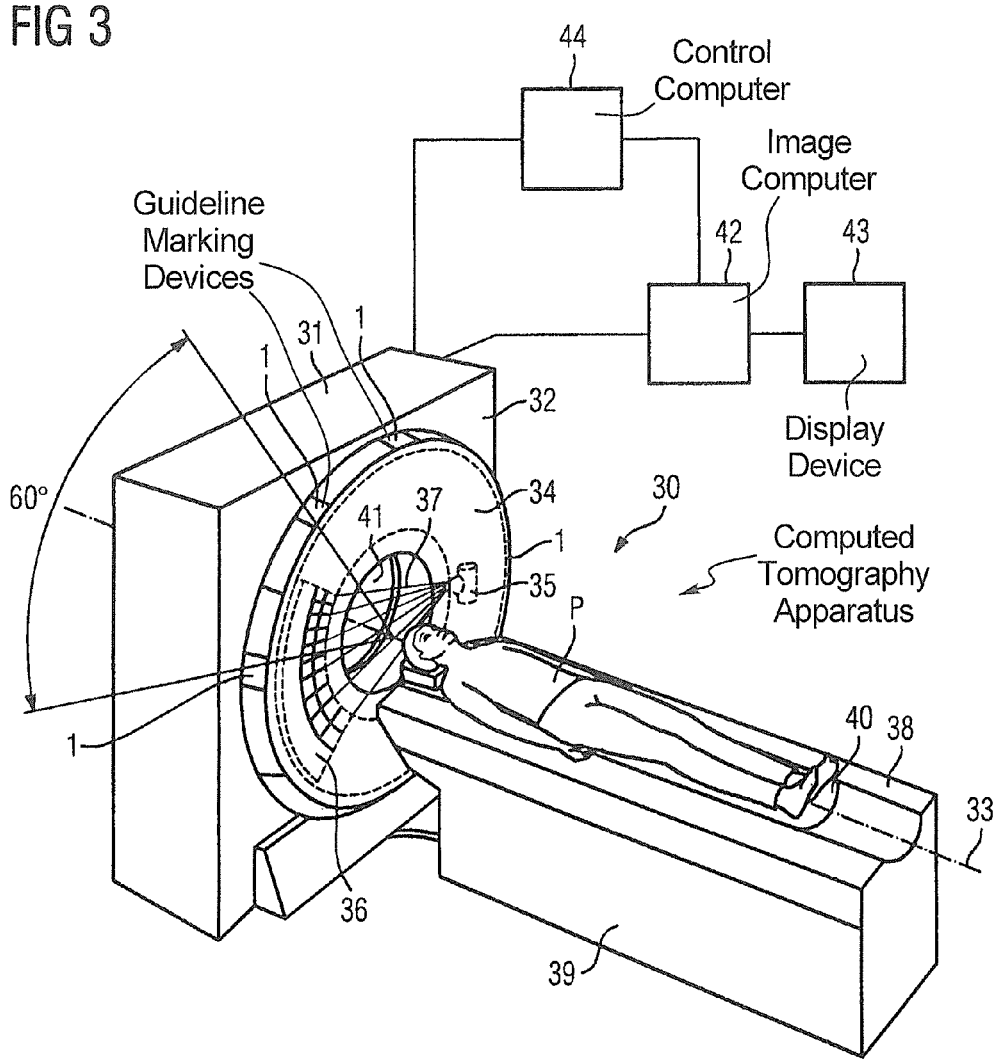
FIG. 3 illustrates a computed tomography apparatus with four devices according to FIG. 2.

A specific realization form of a device from FIG. 1—for example as used in the computed tomography apparatus shown in FIG. 3 to identify planes of a working volume of said computer tomography apparatus—is presented in FIG. 2.

In the exemplary embodiment of the invention that is shown in FIG. 2, the fan laser and the mirror 5 are arranged on a common mount 10. The fan laser is held or supported by a laser receptacle device 11 which is attached to the mount 10, such that said fan laser can rotate around the light source rotation axis. An actuating drive 12 for a specific rotation of the fan laser is associated with said fan laser on its back side.

The mirror 5 with its shaft 9 is held or, respectively, borne by a mirror receptacle device 13 that is attached to the mount 10, which mirror 5 can rotate around the mirror rotation axis 7. An actuating drive 14 for a specific rotation of the mirror 5 is also associated with said mirror 5 or its shaft 9 on its back side. The actuating drives can be electric servomotors, for example. In the exemplary embodiment of the invention that is shown in FIG. 2, the tilt angle $\alpha$ of the surface normal 8 of the mirror plane 6 relative to the mirror rotation axis 7 amounts to approximately 10°.

In the exemplary embodiment of the invention that is shown in FIG. 2, the fan laser and the mirror 5 are arranged on the mount 10 such that the light source rotation axis 4 and the mirror rotation axis 7 are located in one plane. Furthermore, the fan laser is arranged on the mount 10 such its light source rotation axis 4 is bent by approximately 15° (angle $\beta$) relative to the plane E plotted in FIG. 2 (which is situated perpendicular to the plane of the drawing). The mirror 5 is arranged on the mount 10 such that its mirror rotation axis 7 is bent by approximately 25° (angle $\gamma$) relative to the plane E plotted in FIG. 2 (which is situated perpendicular to the plane of the drawing). The light source rotation axis 4 and the mirror rotation axis 7 thus together enclose an angle $\delta$ of approximately 140°, wherein the intersection point S of the light source rotation axis 4 and the mirror rotation axis 7 is situated approximately at the middle point M of the circular disc-shaped mirror 5 or, respectively, the circular disc-shaped mirror surface 6.

As previously noted, the device shown in FIG. 2 is provided for a computed tomography apparatus 30 as is shown in FIG. 3. The computed tomography apparatus 30 has a gantry 31 with a stationary part 32 and with a part 34 rotatable around a system axis 33. In the present exemplary embodiment of the invention, the rotatable part 34 has an x-ray system which comprises an x-ray source 35 and an x-ray detector 36 that are arranged opposite one another on the rotatable part 34. In operation of the computed tomography apparatus 30, x-ray radiation 37 emanates from the x-ray source 35 in the direction of the x-ray detector 36, penetrates a measurement subject and is detected by the x-ray detector 36 in the form of measurement data or measurement signals.

Furthermore, the computed tomography apparatus 30 has a patient bed 38 to support a patient P to be examined. The patient bed 38 has a bed base 39 on which is arranged a patient support plate 40 provided to actually support the patient P. The patient support plate 40 is adjustable relative to the bed base 39 in the direction of the system axis 33 such that it, together with the patient P, can be introduced into the opening 41 of the gantry 31 to acquire 2D x-ray projections of the patient P, for example in a spiral scan. The computational processing of the 2D x-ray projections acquired with the x-ray system and the reconstruction of slice images, 3D images or a 3D data set based on the measurement data or the measurement signals of the 2D x-ray projections takes place with an image computer 42 of the computed tomography apparatus 30, which slice images or 3D images can be presented at a display device 43.

To identify planes in the spatial or working volume before the opening 41, in the exemplary embodiment of the invention four devices (as described in connection with FIG. 2) for the marking of guidelines for medical instruments for interventional procedures on patients (assisted by image information acquired with the computer tomography apparatus 30) are arranged distributed on the front side of the stationary part 32 of the gantry 31 across the upper half-volume of the gantry 31. Two adjacent devices 1 enclose an approximately 60° angle relative to the system axis 33. The arrangement of the devices 1 is such that, without displacement of the devices 1 relative to one another, planes can be identified in a desired manner in the working volume before the opening 41 in order to mark guidelines.

For this purpose, the puncture location for a medical instrument (a puncture needle, for example) and the spatial orientation of the medical instrument are initially established in the course of the procedure planning (by a physician, for example) using slice images of the patient P that are generated and presented on the display device 43, such that this information is available to the image computer 42. Under consideration of the position of the patient or of the patient support plate 40 accommodating the patient in the acquisition of the 2D x-ray projections, and under consideration of the known attachment locations of the devices 1 at the gantry 31, the image computer 42—or another control computer 44 of the computed tomography apparatus 30 to which the information pertaining to the puncture location and the orientation or the guide direction of the puncture needle—can now activate at least two devices 1, in particular the actuating drives for each of the fan laser and the mirror, such that two identifying planes are generated whose intersection line marks the guidance direction for the puncture needle. Furthermore, under consideration of the known attachment locations of the devices on the gantry 31, the patient support plate 40 accommodating the patient can be driven out of the opening 41 so far that the intersection line strikes the body region of the patient P that is to be treated and in particular marks the puncture location.

In contrast to the described exemplary embodiment of the invention, the devices 1 can also be arranged so as to be adjustable on the gantry 31. In this case, two devices on the gantry 31 normally suffice to identify the attitude of planes.

Moreover, the devices 1 can be integrated into the gantry or be arranged on a fore-part of the gantry in the form of a frame or a mount. If the devices 1 are integrated into the gantry 31, at least one window through which the beam fan of a device can exit from the gantry 31 must be provided in the region of each device 1.

The angles indicated in the preceding, in connection with the embodiment of a device 1 or an arrangement of a device 1 on a gantry of a computed tomography apparatus, are moreover to be understood merely as examples, and can also deviate from this depending on the spatial conditions and requirements.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical imaging apparatus comprising:
   an image data acquisition unit configured to interact with a patient to acquire image data from the patient representing a medical image of the patient;
   a first device and a second device configured to operate in combination with each other to identify a plane in space with respect to the patient;
   each of said first and second devices comprising a light source that emits a fan-shaped light beam, said light source being rotatable around a light source rotation axis, and a mirror that reflects the fan-shaped light beam so as to intersect the patient, said mirror being rotatable around a mirror rotation axis and defining a mirror plane, said mirror rotation axis and a surface normal of said mirror plane enclosing an angle that is greater than 0° and less than 90°, said mirror rotation axis and said light source axis being in a common plane and enclosing an angle therebetween in a range between 120° and 160°; and
   a control unit configured to interact with the first and second devices to cause the respective fan-shaped light beams emitted thereby to intersect on a body surface of the patient at a location that is determined from said image data to indicate a location and a direction of a medical instrument for implementing a medical procedure on the patient.

2. A medical imaging apparatus as claimed in claim 1 wherein, in each of said first and second devices, said mirror rotation axis and said surface normal of said mirror plane enclose an angle between 5° and 25°.

3. A medical imaging apparatus as claimed in claim 1 wherein, in each of said first and second devices, said light source is a laser light source.

4. A medical imaging apparatus as claimed in claim 1 wherein each of said first and second devices comprises an actuating drive, operated by said control unit, to rotate said mirror plane around said mirror rotation axis.

5. A medical imaging apparatus as claimed in claim 1 wherein each of said first and second devices comprises an actuating drive, operated by said control unit, to rotate said light source around said light source rotation axis.

6. A medical imaging apparatus as claimed in claim 1 wherein said image data acquisition unit is a computed tomography apparatus.

7. A medical imaging apparatus as claimed in claim 6 wherein said computed tomography apparatus comprises a stationary part and a rotatable part that is rotatable around a system axis of the computed tomography apparatus and wherein said first and second devices are located on said rotatable part.

* * * * *